United States Patent [19]

Letsinger et al.

[11] Patent Number: 5,112,962
[45] Date of Patent: May 12, 1992

[54] LABILE ANCHORS FOR SOLID PHASE POLYNUCLEOTIDE SYNTHESIS

[75] Inventors: Robert L. Letsinger, Wilmette, Ill.; Charles N. Singman, Teaneck, N.J.

[73] Assignee: Northwestern University, Evanston, Ill.

[21] Appl. No.: 612,216

[22] Filed: Nov. 9, 1990

Related U.S. Application Data

[63] Continuation-in-part of Ser. No. 340,347, Apr. 19, 1989, abandoned.

[51] Int. Cl.$^5$ .................. C07H 15/12; C07H 17/00; G01N 33/00; G01N 33/552
[52] U.S. Cl. .................. 536/27; 436/524; 436/527; 436/94
[58] Field of Search .................. 536/27; 436/524, 527, 436/94

[56] References Cited

PUBLICATIONS

Matteucci et al., J. Amer. Chem. Soc., vol. 103: 3185-6 (1981).

Morrison et al., Organic Chemistry, Allyn and Bacon (1973) p. 606.

*Primary Examiner*—Christine Nucker
*Assistant Examiner*—Mindy B. Fleisher
*Attorney, Agent, or Firm*—Tilton, Fallon, Lungmus & Chestnut

[57] ABSTRACT

This invention discloses a linker arm for solid support synthesis of oligonucleotides and oligonucleotide derivatives that allows the oligomers to be released relatively quickly under mild conditions. The linker arm comprises the following:

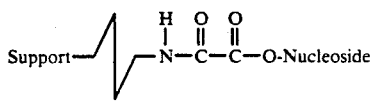

The linker arm releases the oligomer in about one minute to about thirty minutes in a manner that leaves the oligonucleotide fully protected.

15 Claims, 4 Drawing Sheets

LABILE ANCHORS FOR SOLID PHASE POLYNUCLEOTIDE SYNTHESIS

This is a continuation-in-part of copending application Ser. No. 07/340,347 filed on Apr. 19, 1989, abandoned Mar. 15, 1991.

TECHNICAL FIELD

The present invention relates to a method for oligonucleotide synthesis on inorganic solid supports. More particularly, the present invention is related to a linking group that links the oligonucleotide from its terminal 3' hydroxyl group to an ester bond to a primary amine on the solid support. The oligonucleotide can be freed from the solid support in a rapid manner by cleavage with 5% aqueous ammonium hydroxide, triethylamine/alcohol, triethylamine/methanol, or aqueous trimethylamine.

BACKGROUND OF THE INVENTION

Organic polymers have been used as supports during polynucleotide synthesis. Early work is reviewed by Amarnath and Broom, *Chemical Review*, 77:183-217 (1977).

Inorganic polymers are also known in the prior art. Koster, *Tetrahedron Letters*, Vol. 13, 1527-1530 (1972) describes the attachment of nucleoside phosphates to silica gel using a trityl linking group. The method is apparently applicable only to pyridine nucleosides. The cleavage of the nucleoside from the silica support can only be accomplished with acid to which the purine nucleosides are sensitive.

Caruthers, et al. in *Genetic Engineering*, Plenum Press, New York (1982), Vol. 4, p. 1-17; Letsinger, in *Genetic Engineering*, Plenum Press, New York (1985), Vol. 5, p. 191; and Froehler, et al., *Nucleic Acids Research*, 14:5399-5407 (1986) report syntheses of oligonucleotides on inorganic solid supports bearing a succinyl linker arm. See, for example, Matteucci, et al., *Journal of American Chemical Society*, 103:3185-3186 (1981). See FIG. 1A. The succinyl group links the growing oligonucleotide from its terminal 3' hydroxyl group by an ester bond to a primary amine on the support, which may be controlled pore glass (CPG) or silica, by an amide bond. An oligonucleotide is freed from the support after the ester carbonyl group is hydrolyzed by concentrated ammonium hydroxide. For complete cleavage, this reaction needs approximately 3.5 hours at room temperature.

A third generation of DNA synthesizers has been developed that would not only synthesize the oligonucleotide but would also cleave the completed oligonucleotides from the support. However, waiting 3.5 hours before the DNA synthesizer can be utilized is unduly burdensome.

Further, there is growing interest in the synthesis of modified oligonucleotides possessing base sensitive functional groups as "antisense" reagents for inhibiting viral replication. Examples include methyl phosphonate derivatives, shown by Agris et al., Biochemistry (1986) 25, 6268-6275, to inhibit synthesis of vesicular stomatitis viral proteins in virus infected L929 cells and selected oligonucleotide methyl phosphotriester derivatives, reported by Buck et al., Science (1990) 24s, 208-212, to inhibit HIV-1, the causative agent of AIDS. Both the methyl phosphonates and the methyl phosphotriesters are sensitive to the ammoniacal conditions used in conventional work-up of products synthesized on insoluble supports in DNA synthesizers. Indeed, the methyl phosphotriesters are so sensitive that it has not been feasible heretofore to obtain these compounds directly from a solid support. Instead, Buck et al. employed a long, cumbersome strategy that involved: (1) automated synthesis of oligonucleotide, β-cyanoethyl phosphotriester derivatives on solid CPG supports using DMT-N-protected (benzoyl and isobutyryl) nucleoside β-cyanoethyl phosphoramidites, (2) cleavage from the support (succinyl anchor) by concentrated ammonium hydroxide to yield the unprotected oligonucleotide phosphodiesters, (3) reprotection of the purine and pyrimidine amino groups with 9-fluorenylmethoxycarbonyl, (4) methylation of the phosphodiester groups using methanol and toluenesulfony chloride (a relatively inefficient process), and (5) cleavage of the 9-fluorenylmethoxycarbonyl groups using triethylamine. Steps 3≈5 must be carried out manually in solution after the oligomer has been removed from the support.

Another family of potentially interesting oligonucleotide analogues are derivatives with unsubstituted internucleoside phosphoramidate links (O=PNH$_2$) Procedures for synthesis of very short oligomers of this type in solution have been reported (Tomasz, et al., *Tetrahedron Letters*, 22:3905-3908, (1981); Letsinger, et al, *Nucleic Acid Research*, 4:3487-3499 (1986); however, as reported by Tomasz et al., these compounds are sensitive to the strong ammonical conditions employed in cleaving succinyl anchors used in solid support synthesis.

There is a need for a linker arm that allows an oligonucleotide or substituted oligonucleotide to be cleaved quickly from the support under milder conditions than employed with the succinyl derivatives.

Matteucci, et al., ibid, introduced the succinyl linker arm for DNA synthesis in 1980. The linker arm is attached to the support by an alkaline resistent amide bond and to the nucleoside through an alkaline labile ester bond. In an effort to improve the cleaving ability of the succinyl group, one skilled in the art would likely increase the lability of the succinyl linker group by increasing the electron withdrawing potential of the spacer chain between the two carbonyl groups. The increased lability would result in making the carbonyl carbon more electrophilic and therefore more susceptible to nucleophilic attack by ammonium hydroxide. Schott and Letsinger in an unpublished work at Northwestern University introduced an electron withdrawing group within the hydrocarbon spacer of the linker. A diglycolyl linker arm was synthesized as shown in FIG. 1B. The electron withdrawing nature of the central oxygen atom in the spacer chain would be expected to make the carbonyl carbon more electrophilic, and thus would create a more alkaline labile ester group. It was found that the nucleosides attached to the diglycol linker arm were liberated slightly faster (35% faster) than when attached to the succinyl linker arm, but the increase was not sufficient to enable base labile oligonucleotide derivatives to be removed selectively. Simple inductive activation by the electronegative oxygen in an ether function was not sufficient.

SUMMARY OF THE INVENTION

The present invention provides a new and useful linker arm for the chemical synthesis of any deoxyribonucleic acid (DNA) or ribonucleic acid (RNA) or modified derivative which contain any deoxynucleotides, nucleotides, polynucleotides and polydeoxynucleotides, as well as polypeptides attached to (deoxy) nucleotides.

The linker arm used in the present invention is based upon an oxalyl ester. See FIG. 1. In the figure, CPG refers to a controlled pore glass support and DMT refers to dimethyoxytrityl; B refers to a nucleobase. Any nucleoside may be attached to the linker arm through one of its hydroxyl groups. The key feature is the high reactivity imparted to an ester by an adjacent α-carbonyl group. Among the dicarboxylic acid esters, the derivatives of oxalic acid are unique since they are the only ones possessing neighboring carbonyl functions. As a consequence of stereoelectronic effects related to this positioning, the ester linkage becomes much more susceptible to cleavage by nucleophiles such as hydroxide, methoxide, ammonia, and primary and secondary amines. On the other hand this ester linkage is stable to the tertiary amines used in DNA and RNA synthesis (e.g. pyridine or lutidine); so the growing oligonucleotide is not cleaved from the support prematurely.

A variety of solid supports can be employed in the present invention and these include, for example, silica, porous glass, aluminosilicates, borosilicates, metal oxides such as aluminium and nickel oxide, iron oxide and various clays, and cross-linked polystyrene and polyamides. The solid support should be relatively chemically inert to the reagents used in synthesis of the nucleic acids except for the reactivity required in anchoring the initial nucleoside to the support.

The oxalyl linker can be initially reacted either with a solid support (FIG. 2, method) or the nucleoside (scheme 2). The processes of the present invention are practiced by treatment of nucleosides as shown in the synthetic scheme for the synthesis of an oxalyl support in FIGS. 2 and 4. A series of sequential steps whereby the series results in the addition of an appropriately protected nucleoside to the support are shown as follows:

Method 1

(A) Treatment of oxalychloride with a nucleophilic base, preferably triazole;
(B) Treatment of amine containing support with product of A;
(C) Treatment of product B with appropriately protected nucleoside;
(D) Capping of underivatized sites on the support.

Method 2

(1) Treat appropriately protected nucleoside with product of A;
(2) Treat amine containing support with product of 1;
(3) Cap underivatized sites on the support.

The nucleoside is added to the solid support by repetition of steps B, C and D or 1, 2 and 3 until the desired amount of nucleoside is linked to the support, after which the nucleoside loaded support is used for synthesis of the oligonucleotides. The oligonucleotide is then removed from the support by subjecting the oxalyl linker arm to basic conditions, such as ammonium hydroxide in methanol (e.g. 5% ammonium hydroxide), dilute ammonium hydroxide, primary or secondary amines in alcohols, triethylamine/alcohol, triethylamine/ethanol, wet triethylamine, triethylamine/methanol, trimethylamine/water (40:100, v/v), or water at a pH greater than 8.5. The oxalyl linker is very rapidly cleaved by the forgoing reagents so that the removal of the nucleoside or oligonucleotide is obtained in a relatively short period of time ranging from about two to about 30 minutes, which is substantially less than the hours necessary to cleave a nucleoside loaded succinyl support. The base should be selected so that it is compatible with the oxalyl linker arm and oligonucleotide so that cleavage occurs in an effective amount of time, preferably, about one minute to about three hours, more preferably, about two minutes to about 30 minutes.

FIGURES IN THE DRAWINGS

Other advantages of the present invention will be readily appreciated as the same becomes better understood by reference to the following detailed description when considered in connection with the accompanying drawings wherein:

FIG. 1A shows a conventional succinyl linker arm;
FIG. 1B shows a diglycolyl linker arm;
FIG. 1C shows the oxalyl linker arm of the present invention;
FIG. 2 shows the schematic process for the synthesis of an oligonucleotide linked to a solid support by the oxalyl linker arm of the present invention;
FIG. 3 shows the comparison of temperature dependence of dissociation of the complex formed between an oligonucleotide [d(AATCTGCAGGTTG)], synthesized either via an oxalyl or a succinyl linker arm, and the complementary oligonucleotide. This experiment demonstrates that the oxalyl anchor affords oligonucleotides comparable to those prepared with the succinyl anchor; and
FIG. 4 shows a schematic process for the synthesis and recovery of a fully protected oligonucleotide via an oxalyl linker arm support.

DETAILED DESCRIPTION OF THE DRAWINGS

As indicated, the solid support employed in the present invention can be chosen from a wide variety of supports, for example, silica, porous glass, aluminosilicates, borosilicates, metal oxides such as aluminum, iron and nickel oxide in various clays, and organic cross-linked polymers. The support is linked to the nucleoside by the oxalyl linker arm which is readily hydrolyzable at the point of attachment to the nucleoside, preferably with a weak base such as ammonium hydroxide, ammonium hydroxide in methanol, triethylamine/alcohol, triethylamine/ethanol, methylamine or dimethylamine, triethylamine/methanol or trimethylamine/water. The oxalyl linker arm can be attached to the support by covalent bonding to a primary or secondary amine on the support.

The oxalyl linker arm comprises the formula:

wherein R' equals a nucleoside fragment and R", the soluble support.

Figure 1A:
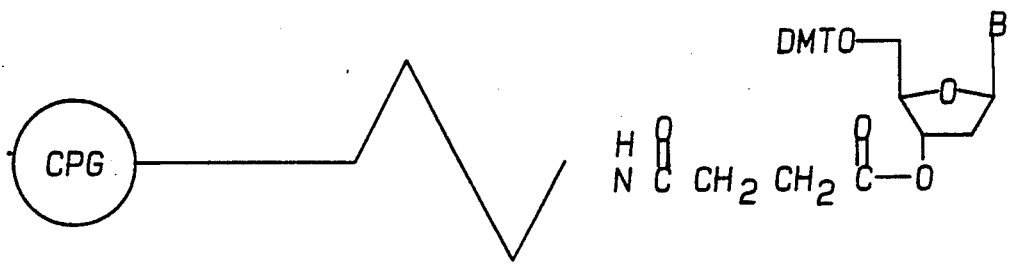
Figure 1B:
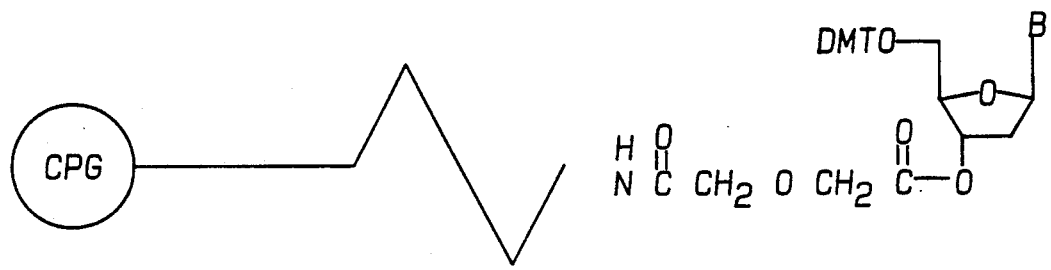
Figure 1C:
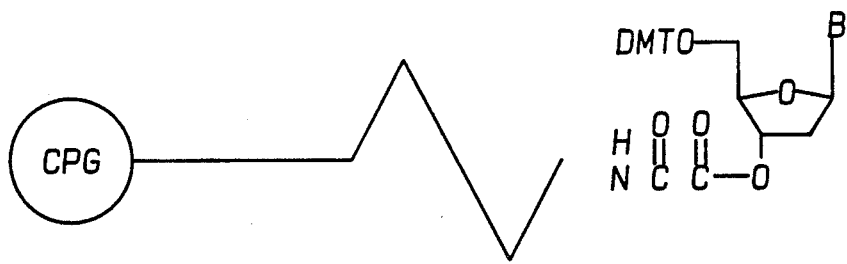
Figure 2:
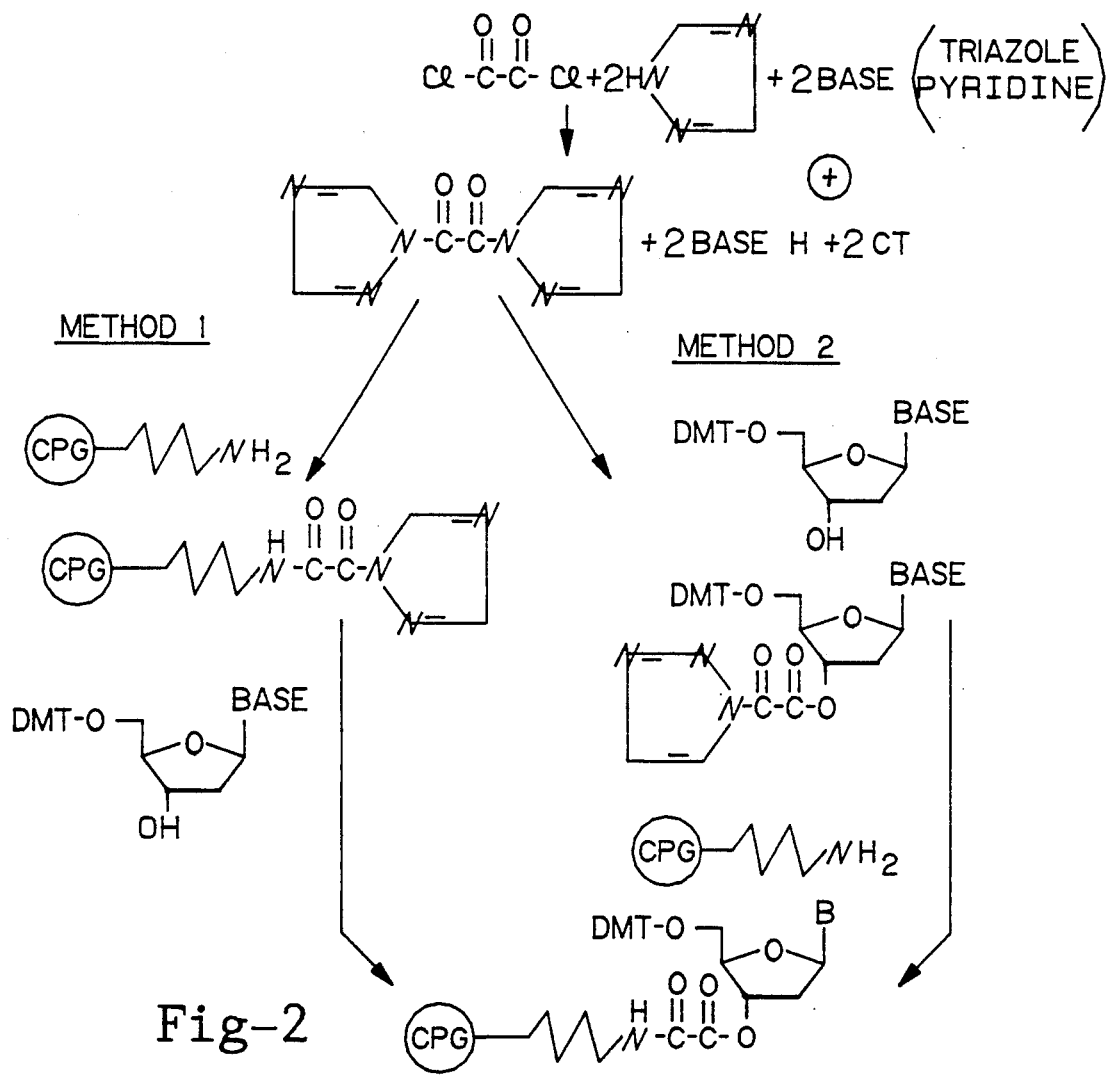

The solid support can be attached to a nucleoside by reacting an activated oxalyl derivative (e.g. oxalyl triazolide, RC(O)C(O)R, FIG. 2) with amine groups on a solid support, forming an amide linkage. The resulting modified support is then treated with the desired nucleoside, forming an ester linkage with the nucleoside, and any unreacted amine groups on the support are then blocked by an appropriate reagent (e.g. acetic anhydride).

Alternatively, the active oxalyl reagent may be reacted first with the desired nucleoside to form the ester linkage, followed by reaction with the amine groups on the support to form the amide linkage.

Preferably, the nucleoside is linked to the support through the 3'—OH group of a nucleoside protected at the 5'—O position. On unblocking the 5'—O, this position becomes available for linkage to other nucleosides for chain elongation. For syntheses in the 5'→3' direction, linkage of the initial nucleoside at the 5'—O is also feasible.

The capping on the support reaction involves the blocking or capping of other reactive moieties in order to prevent the formation of several oligonucleotides with heterogeneous sequences. This capping step can be performed by treating the derived support with blocking agents, e.g. dimethylaminopyridine and acetic anhydride.

Other traditional blocking groups that can be employed are acid anhydrides such as acetic anhydride.

Generally, FIG. 2 represents loading of a representative oligonucleotide, 5,—O-dimethoxytrityl-2'-deoxynucleoside-3' via an oxalyl linker arm. While a variety of solid supports can be utilized, controlled pore glass (CPG) is shown in the schematic of FIG. 2. In the process, a commercial aminoalkyl-CPG support is derivatized with the oxalyl linker arm and one of the four different nucleosides (db$_2$A, db$_2$C, dibG, and dT) in separate reactions. Oxalyl chloride, which is typically used to form the oxalyl linker arm in the present invention, is converted to a less reactive triazolide derivative with triazole in CH$_3$CN in a separate flask. In method 1 (FIG. 2) the solid support is then treated successively with the oxalyl triazolide and the 5'-O-DMT-nucleoside. This treatment is followed for two cycles, which affords a CPG support loaded to the extent of 16 to 22 micro moles/gm (CPG) (d(A)=18, d(C)=22, d(G)=16, and T=20). The unreacted amine groups on the CPG support can then be capped by treating the derivatized support with conventional blocking agents such as acetic anhydride with a catalyst. Typically, the synthesis of a nucleoside loaded oxalyl support can be completed in about one to about eight hours, which is substantially less than the time used in synthesizing nucleoside loaded succinyl support.

The lability of the oxalyl linker arm is the key to the invention. The oxalyl linker arm is stable to pyridine used in oligonucleotide synthesis. The oxalyl linker can be rapidly cleaved by 5% ammonium hydroxide in methanol, ammonium hydroxide, wet tertiary amine, triethylamine/alcohol, triethylamine/methanol, triethylamine ethanol, aqueous trimethylamine and other bases. Table 1 lists relative cleavage times for three bases.

TABLE 1

| Cleavage Rates of the Oxalyl Linker Arm | |
|---|---|
| Base | Time for Complete Cleavage |
| NH$_4$OH | Less than 5 minutes |
| Wet Triethylamine | 5 minutes |
| Wet Trimethylamine | 10–15 minutes |

As can be seen by the short cleavage times, the oxalyl linker can be useful in the synthesis and recovery of protected or unprotected oligonucleotide blocks.

Cleavage times as noted are relatively short. They may range from about one minute to about three hours, depending on the base utilized and oligonucleotide. Preferably, cleavage ranges from about two minutes to about 20 minutes.

Other conditions favorable to the cleavage action include pH range conducive to the cleavage action, preferably above about pH 8.5. Further, the cleavage may take place at temperatures ranging from about 10° C. to about 60° C. Preferably, cleavage takes place at about 20° C. to about 30° C., more preferably, at room temperature. The mild conditions required for the extremely fast cleavage rates with the linker arm of the present invention provide an efficient method of oligonucleotide production.

The invention is illustrated in detail by means of the following examples.

EXAMPLE 1

Synthesis of 5'-O-Dimethoxytrityl-2'-Deoxynucleoside 3'-O-CPG with an Oxalyl Linker Arm (Method 1)

This example shows a detailed synthesis of the production of the title compound by the schematic process shown in FIG. 2 (Method 1).

This procedure was used to synthesize oxalyl linked CPG supports with each of the four DMT protected 2'deoxynucleosides (d(DMTA), d(DMTC) d(DMTG), DMT(T)). Typically, the CPG (1gm, 80–120 mesh, 500A) was placed into a Glenco 5.0 ml gas tight syringe with a glass wool plug at the inlet. Washes were effected by drawing up the desired amount of the reagent, resuspending the support by hand agitation, and ejecting the solution. The CPG was initially washed with CH$_3$CN (4×4 ml) and dry CH$_3$CN (6×4 ml). In a separate flask capped with a septum, triazole (500mg., 6.0 mmol) was dissolved in pyridine/CH$_2$Cl$_2$ (4 ml, 1/1, v/v). To this solution oxalyl chloride (200 micro liters, 2.2 mmol) was added carefully (a vigorous reaction occasionally occurred). A small amount of a precipitate always formed but this was typically less than 5% of the volume. When the reaction was attempted with either pyridine or imidazole nearly the entire volume of the flask was occupied by the precipitate, which precluded use of the reagent. The oxalyl imidazodide solution (3 ml) was drawn into the syringe. The syringe needle was capped with a cork. After 30 minutes, the solution was ejected from the syringe and the CPG was rinsed with dry CH$_3$CN (3×3 ml). A 5-O-DMT protected nucleoside (300 mg, 0.46-0.5 mmol) and N,N-dimethylaminepyridine (20 mg) had been previously dissolved in dry pyridine/CH$_2$Cl$_2$ (3 ml, 1/2, v/v). This solution was drawn into the syringe and allowed to react for two hours. The solution was then ejected from the syringe and the support was washed with pyridine (4×3 ml), CH$_2$Cl$_2$ (4×3 ml), and diethyl ether (3×3 ml) and then air dried.

For assay of the loading, a small aliquot of the nucleoside loaded support (10 mg) was removed and suspended in 5 ml of a 3% trichloraetic acid/nitromethane (v/v). The solution immediately turned orange. The concentration of the DMT cation (lambda min =498, max =79000) was determined and the loading of the nucleoside on the CPG was calculated. The values ranged from 7 to 14 230 m/mg of CPG (d(A)=8, d(C)=12, d(G)=7, and T=11). This value was lower than desired so the CPG was treated a second time with the reactants, beginning at the initial CH$_3$CH wash. Loading values then ranged from 16 to 24 230 m/gm (GPC) (d(A)=18, d(C)=22, d(G)=16, and T=20). The unreacted amine groups were capped using a binary reagent: DMAP in Pyr/THF (0.3 M, 1/15, v/v. 2.0 ml) was drawn into the syringe immediately followed by Ac$_2$O/THF (0.6 M, 1.0 ml), and the mixture agitated for one minute. The capping reagents were ejected from the syringe, and the CPG was washed with Pyr/CH$_3$CN (1/4, v/v, 4×4 ml), CH$_3$CN (4×4 ml), diethyl ether (4×3 ml) and then air dried. The nucleoside loaded supports were stored in Drierite desiccators.

EXAMPLE 2

Synthesizing of Oligonucleotides on a Support Prepared by Method 1.

To demonstrate that oligonucleotide chains can be prepared on a support employing an oxalyl anchor, two different oligonucleotides were synthesized. For comparison, each sequence was also prepared using the same chemistry with conventional CPG supports having a succinyl linker.

The syntheses were carried out in a Biosearch 8600 DNA synthesizer following the version 4.3 protocol listed in Chapter I of the Biosearch instruction manual provided with the synthesizer. At the completion of the synthesis using an oxalyl support, the support with the bound oligonucleotide was transferred to a vial for cleavage. Concentrated NH$_4$OH (1.0 ml) was added to the vial, which was capped and allowed to stand for five minutes. For characterization, the solution containing the released oligonucleotide derivatives was then transferred to a second vial, which was capped and heated at 55 degrees Centigrade for five hours to remove the base protecting groups. The oligonucleotide products were then recovered by lyophilization.

At the completion of the synthesis involving a succinyl linker, the support bound oligomers were transferred to a vial for cleavage and deprotection. Concentrated NH$_4$OH (1.0 ml) was added and the vial was heated at 55° C. for five hours. After cooling, the NH$_4$OH solution was separated from the support by filtration, and the support was washed with three portions of water (1.0 ml). The solutions were combined and the crude product was obtained by lyophilization.

TABLE 2

Summary of Pertinent Data for Oligonucleotides Synthesized on Oxalyl and Succinyl Supports

| OLIGONUCLEOTIDE | HPLC$^a$ (min) | AVG. COUPLING$^b$ YIELD % | CRUDE RECOVERY A$_{260}$ UNITS |
|---|---|---|---|
| d(AATCTGCAGGTTG) | | | |
| Succinyl | 15.2 | 99.4 | 83 |
| Oxalyl | 15.2 | 98.7 | 75 |
| d(CAACCTGCAGATT) | | | |
| Succinyl | 20.8 | 99.0 | 88 |
| Oxalyl | 20.8 | 101 | 72 |

$^a$IBM C-18, 0.1 M TEAA buffer pH 7.1, initial 1% CH$_3$CH increasing at 1%/minute. Elution times are reported in minutes.
$^b$Based on DMT cation.

The two sets of oligonucleotides (see Table 2) were purified by HPLC (IBM C-18, 4.6×20 cm column, using 1.0 M TEAA buffer, pH 7.1; starting at 1% CH$_3$CN increasing at 1%/minute). As can be seen from Table 2, the elution times were the same for a given sequence and there was no significant difference in coupling yields for syntheses conducted on the oxalyl and succinyl supports (average, 98.5% per coupling). With the oxalyl supports, however, the trityl yield exceeded 100% for the first two or three couplings, indicative of the presence of some reactive sites not measured by the initial DMT test.

Figure 3:
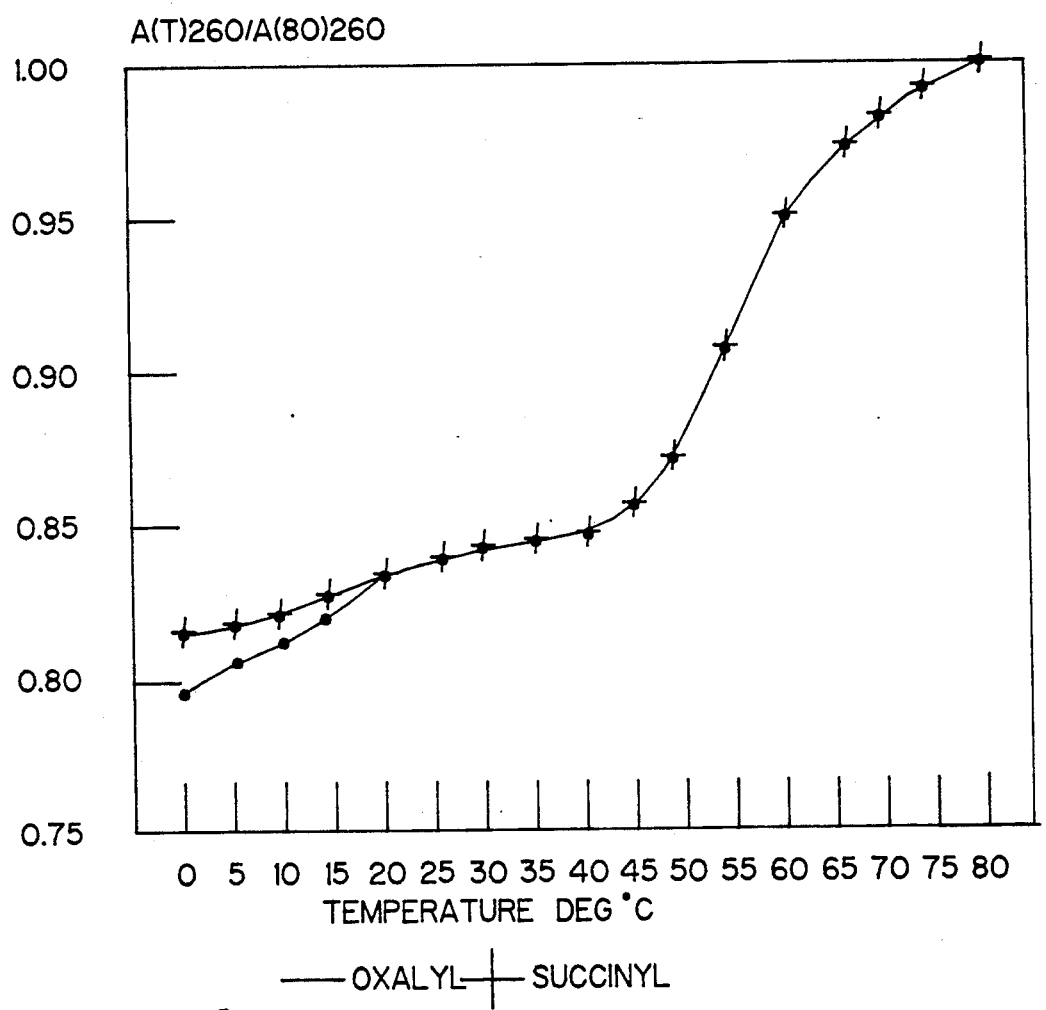

As a test of fidelity in the syntheses, a binding study was performed with the pairs of complementary oligonucleotides synthesized independently on the oxalyl-CPG and succinyl-CPG. It is well established that even one mismatch in base pairing in short duplexes of this type leads to a significant decrease (20° C.) in the Tm value (temperature corresponding to half dissociation of the complex, at equilibrium). The data in FIG. 3 show that the Tm values for the complexes formed the two sets of complementary oligonucleotides [d(AATCTGCAGGTTG)] and [d(CAACCTGCAGATT)] are identical (Tm=55° C.), showing that the same oligomers were obtained from the syntheses conducted on the oxalyl-CPG on one hand and on the conventional succinyl-CPG on the other.

The results indicate that there is no difference in the quality of the oligonucleotides synthesized on the oxalyl and succinyl supports. However, the oxalyl support of the present invention has the advantage that it can be cleaved rapidly under mild conditions. This provides for a shortened time requirement to cleave oligonucleotides from their support in machine synthesis and opens the way to synthesizing oligomers containing base labile groups.

EXAMPLE 3

Synthesis of CPG Support by Method 2

In a 10 ml flask capped with a septum, 1,2,4-triazole (77 mg, 1.12 mmol) was dissolved in acetonitrile (2 ml). To this solution oxalyl chloride (0.02 ml, 0.225 mmol) was added. A small amount of precipitate formed but disappeared after adding pyridine (0.1 ml). 5'-O-DMT-Guanosine (1440 mg. 0.225 mmol) in acetonitrile (1 ml) and pyridine (0.5 ml) was added and the mixture was allowed to sit for an hour.

NH$_2$-CPG support (400 mg) was dried by dry acetonitrile (5 ml×3) in a 10 ml syringe and treated with the solution above for five minutes. The solution was then ejected from the syringe and the support was washed with pyridine (5 ml ×3) and capped by capping solution containing DMAP in pyridine/THF (0.25 M, 1/15, v/v, 2.5 ml) and acetic anhydride (0.6 M, 2.5 ml) for two minutes. After capping, the oxalyl support was washed with pyridine/acetonitrile ($\frac{1}{4}$, v/v, 5 ml ×2) and acetonitrile (5 ml ×3).

For assay of the loading, a small aliquot of the dG loaded support (about 10 mg) was removed and treated with 5 ml of 3% DCA in dichloromethane. The concentration of DMT cation (lambda max=447, epsilon=4900) was determined and the loading of the dibG on the CPG supported was calculated to be 35.8 μmoles/gram.

EXAMPLE 4

Relative Reactivity of Oxalyl and Succinyl Linkers

Lability of the oxalyl linker (formed by Method 2) and succinyl linker to concentrated ammonia and trimethylamine (40% in water) was assayed using a DMT-ibG loaded support. A series of aliquots (about 10 mg) of the support was placed in a syringe and treated with the basic solution for a specified time, then the support was treated with 5ml of 2.5% DCA in dichloromethane. The concentration of DMT cation was measured and the cleavage percentage was calculated. Table 3 gives the cleavage percentage of the oxalyl and succinyl linker arm by bases in a defined time.

TABLE 3

Lability of Succinyl and Oxalyl Linker Arm to Concentrated NH4OH and Trimethylamine

| Support | Concentrated NH4OH | | Trimethylamine 40% In Water | | |
|---|---|---|---|---|---|
| | 5 min | 1 min | 15 min | 5 min | 1 min |
| Oxalyl | 100 | 100 | 100 | 100 | 95.4 |
| Succinyl | 12.2 | 4.1 | 9.8 | 3.4 | |

EXAMPLE 4

S is of Fully Protected Trimer
$d(A^{BZ}(OCH_3)C^{BZ}(OCH_3)G^{BZ})$

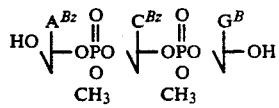

In order to demonstrate that the oxalyl support can be used to synthesize oligonucleotides containing base labile groups, the above trimer was synthesized. The foregoing trimer cannot be synthesized on a succinyl support because the protective groups and the methyl phosphotriester groups are sensitive to the concentrated ammonia needed to cleave the succinic ester.

Figure 4:
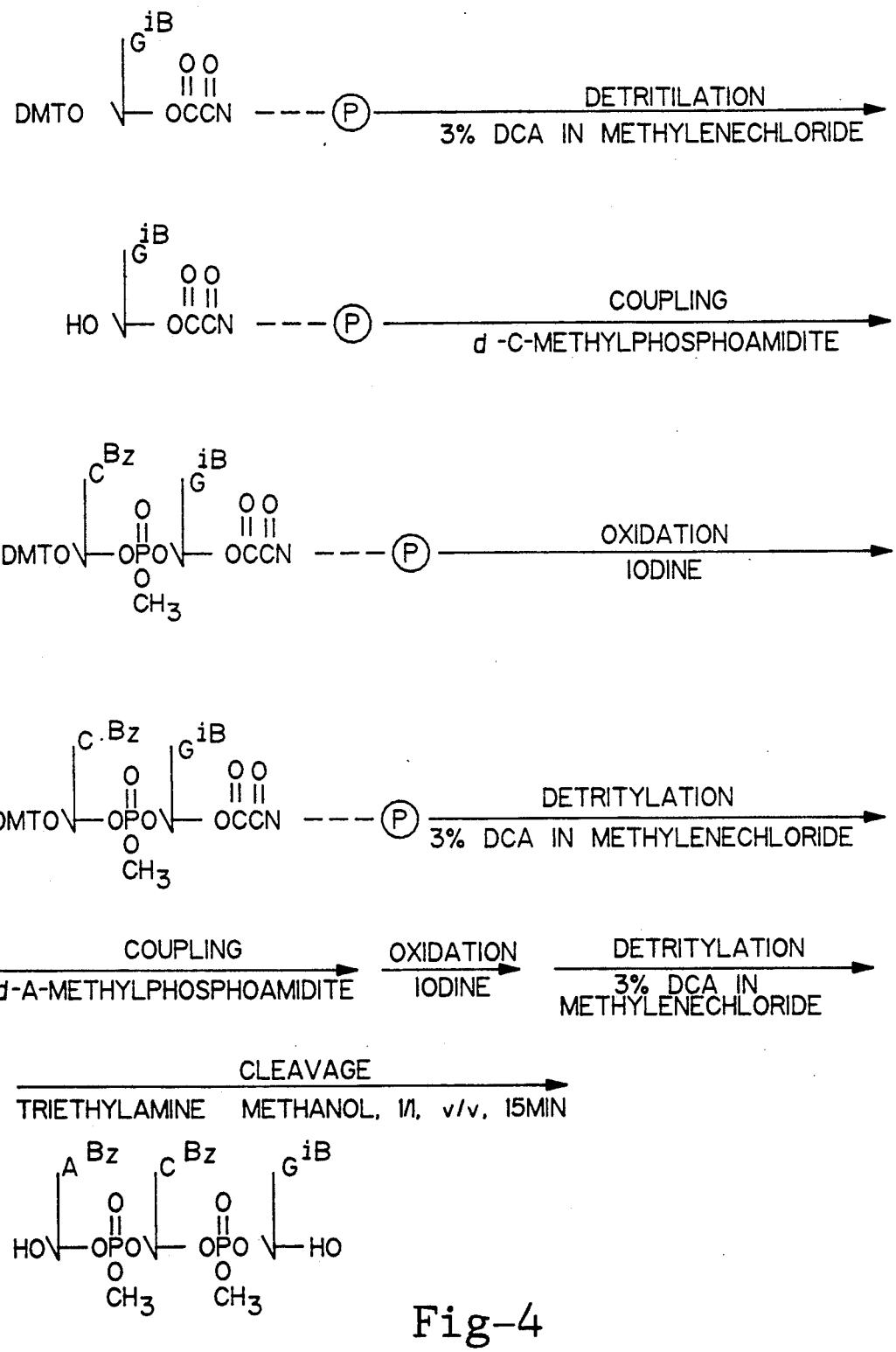

The syringe technique of Taneka and Letsinger, Nuc. Acids. Res., 98:3655–3657 (1982), and methyl phosphoramidite chemistry were used in the synthesis of the fully protected trimer. The general scheme for the solid support synthesis chemistry appears in FIG. 4.

The DMT-bzG loaded oxalyl support (50 mg, 1.8 umol prepared by Method 2), was poured into a 2.5 ml Glenco Gas tight syringe with a glass wool plug at the inlet. Washes were effected by drawing up the desired reagent, resuspending the support by brief hand agitation, and ejecting the solution. The DMT protecting group was removed by washing with 5 ml of 3% DCA in methylene chloride. The orange effluents were pooled for subsequent spectroscopy (448 nm) and calculation of bound DMT-nucleoside. The support was washed successively with pyridine/acetonitrile (4/1, v/v, 1×1 ml) and dry acetonitrile (4×1 ml). The dC-methyl phosphoramidite reagent (40 mg) and tetrazole (16 mg) in acetonitrile (1 ml) was then drawn up into the syringe, which was agitated slowly for 2 minutes. The coupling reagents were ejected from the syringe, and the support was washed with pyridine/acetonitrile (4/1, v/v, 2×1 ml). An iodine solution (0.1 M in THF/pyridine/water, 80/18/2, v/v/v, 1 ml) was drawn into the syringe to oxidize the phosphite intermediate (2 minutes). The oxidant was ejected and the support was washed with pyridine/acetonitrile (¼, v/v, 2×1 ml) and acetonitrile (2×1 ml) to complete the cycle, giving a fully protected dimer. Another reaction cycle with dA-phosphoramidite reagent gave the fully protected trimer bound to the support. For cleavage of the oligonucleotide from the support, a mixture of triethylamine and methanol (1/1, v/v) was drawn into the syringe, and 15 minutes later, ejected into a 25 ml flask. Some methanol was drawn into the syringe to wash the support and ejected into the same flask. The solvent was removed in two minutes by a rotary evaporator to give 67.5 A260 units of crude material. The support left in the syringe was treated with triethylamine/methanol (1/1, v/v) for another 30 minutes in order to determine how much nucleotidic material was left after 15 minutes of treatment. Only 5 A260 units of material was found. The crude trimer was purified by preparative TLC (Brinkman, 10×20 cm, layer 0.25 mm) using ethyl acetate/methanol (3/2, v/v) as eluent, giving 21 A260 units of purified trimer.

The trimer 8 was characterized by mass spectrum (FIG. 16), HPLC (FIG. 19) and TLC (FIG. 18).

The trimer derivative bearing the base protecting groups and the methyl phosphotriester links was characterized by the FB+ mass spectrum (molecular ion, 1176), HPLC (elution time 29.4 minutes; C-18 phase column, water with an acetonitrile gradient increasing at the rate of 1% acetonitrile/minute, flow rate 0.5 ml/minute) TLC (Rf 0.5; Brinkman silica plate; ethyl acetate/methanol 3/2 v/v), and deprotection to give d(ACG) by treatment with concentrated ammonium hydroxide at 55° C. for 5 hours (HPLC elution time 8.9 minutes, identical with a sample of d(ACG) prepared on a succinyl-CPG support in the standard way; HPLC was carried out under the same conditions employed for the fully protected trimer).

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims the invention may be practiced otherwise than as specifically described.

What is claimed is:

1. A linker arm for solid support oligonucleotide synthesis comprising:

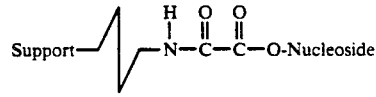

2. A process for attaching a solid support to a nucleoside comprising reacting an active oxalyl derivative of the formula

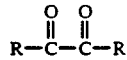

where R equals triazole, a representative of a good departing group for good nucleophilic attach on an aryl derivative, with amine groups of an appropriate solid support, forming an amide linking;

treating the solid support with a desired nucleoside, forming an ester linkage;

and blocking any unreacted amine groups from the solid support by the addition of blocking groups.

3. The process of claim 2, wherein the departing group is triazole or triazolide.

4. The process of claim 2, wherein the amount of time needed to derivatize the solid support with the nucleoside is about one to about eight hours.

5. A process for attaching a solid support to a nucleoside comprising reacting an oxalyl derivative of the formula:

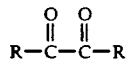

wherein R is a good departing group, with an OH of a desired nucleoside to form an ester linkage;

treating amine groups of a solid support with the derivatized nucleosides to form an amide linkage; and blocking any unreacted amine groups from the solid support by the addition of blocking groups.

6. The process of claim 5, wherein the nucleophilic base is triazole or triazolide.

7. The process of claim 5, wherein the amount of time needed to derivatize the solid support with the nucleoside is about one half to about eight hours.

8. A process for cleaving an oligonucleotide or an oligonucleotide derivative from a solid support wherein the oligonucleotide is attached to the solid support by a linker arm comprising the formula:

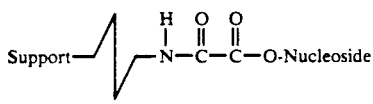

comprising the steps of treating the oligonucleotide or oligonucleotide derivative with a cleaving agent at pH of at least about 8.5 for the effective amount of time to cleave the oligonucleotide from the solid support.

9. The process of claim 8, wherein the cleaving agent is selected from the group consisting of $NH_4OH$, $NH_4OH$ in an alcohol, a tertiary amine (wet), triethylamine (wet), triethylamine/alcohol, triethylamine/methanol, triethylamine/ethanol, trimethylamine/$H_2O$.

10. The process of claim 9, wherein the cleaving agent is a solution of triethylamine/methanol.

11. The process of claim 8, wherein the oligonucleotide or derivative is treated by the cleaving agent for an amount of time ranging from about one minute to about 30 minutes.

12. The process of claim 8, wherein the oligonucleotide or derivative is treated by the cleaving agent for an amount of time ranging from about one minute to about three hours.

13. The process of claim 9, wherein the oligonucleotide or derivative is cleaved from the solid support at a temperature ranging from about 10° C. to about 60° C.

14. The process of claim 9, wherein the oligonucleotide or derivative is cleaved from the solid support at a temperature ranging from about 20° C. to about 30° C.

15. The oligonucleotide of the process of claim 10 with base labile groups.

* * * * *